(12) United States Patent
McFerran

(10) Patent No.: US 8,636,714 B2
(45) Date of Patent: Jan. 28, 2014

(54) MICROCATHETER WITH SLEEVED GUIDEWIRE PORT

(75) Inventor: Sean McFerran, Newark, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1470 days.

(21) Appl. No.: 10/667,056

(22) Filed: Sep. 22, 2003

(65) Prior Publication Data

US 2005/0065498 A1  Mar. 24, 2005

(51) Int. Cl.
*A61M 25/00* (2006.01)

(52) U.S. Cl.
USPC ........................................ 604/523; 604/96.01

(58) Field of Classification Search
USPC ............. 604/103.04, 164.13, 167.01, 167.02, 604/167.03, 167.04, 103, 96.01, 164.01, 604/523–532, 95.01, 95.05
See application file for complete search history.

(56) References Cited

U.S. PATENT DOCUMENTS

| | | | |
|---|---|---|---|
| 1,719,428 A * | 7/1929 | Friedman | 604/105 |
| 4,657,536 A | 4/1987 | Dorman | |
| 4,932,413 A | 6/1990 | Shockey et al. | |
| 4,947,864 A | 8/1990 | Shockey et al. | |
| 5,030,210 A * | 7/1991 | Alchas | 604/247 |
| 5,091,205 A | 2/1992 | Fan | |
| 5,135,535 A | 8/1992 | Kramer | |
| 5,156,594 A | 10/1992 | Keith | |
| 5,281,203 A | 1/1994 | Ressemann | |
| 5,306,247 A * | 4/1994 | Pfenninger | 604/102.02 |
| 5,342,301 A | 8/1994 | Saab | |
| 5,360,330 A | 11/1994 | Jensen et al. | |
| 5,387,226 A | 2/1995 | Miraki | |
| 5,415,639 A | 5/1995 | VandenEinde et al. | |
| 5,449,362 A | 9/1995 | Chaisson et al. | |
| 5,501,667 A | 3/1996 | Verduin, Jr. | |
| 5,540,236 A | 7/1996 | Ginn | |
| 5,645,533 A | 7/1997 | Blaeser et al. | |
| 5,690,613 A | 11/1997 | Verbeek | |
| 5,690,644 A * | 11/1997 | Yurek et al. | 623/1.11 |
| 5,709,658 A | 1/1998 | Sirhan et al. | |
| 5,738,667 A | 4/1998 | Solar | |
| 5,807,349 A * | 9/1998 | Person et al. | 604/247 |
| 5,807,355 A | 9/1998 | Ramzipoor | |
| 5,817,053 A | 10/1998 | Agarwal | |
| 5,824,173 A | 10/1998 | Fontirroche et al. | |
| 5,843,050 A | 12/1998 | Jones et al. | |
| 5,876,375 A | 3/1999 | Penny | |
| 5,919,175 A | 7/1999 | Sirhan | |

(Continued)

FOREIGN PATENT DOCUMENTS

WO    WO 00/69500 A1    11/2000

OTHER PUBLICATIONS

U.S. Appl. No. 10/653,375 to Mark S. Holzapfel et al., filed Sep. 2, 2003.

*Primary Examiner* — Kevin C Sirmons
*Assistant Examiner* — Phillip Gray
(74) *Attorney, Agent, or Firm* — Seager, Tufte & Wickhem LLC

(57) ABSTRACT

A microcatheter having a guidewire port that is positioned proximal of the distal end of the microcatheter in order to provide rapid exchange capability. The guidewire port includes provisions that permit guidewire access into a lumen of the microcatheter while providing a relatively fluid tight seal at least when the guidewire is not present in the guidewire port.

15 Claims, 5 Drawing Sheets

(56) References Cited

U.S. PATENT DOCUMENTS

| | | |
|---|---|---|
| 5,921,971 A | 7/1999 | Agro et al. |
| 5,947,927 A | 9/1999 | Mertens |
| 5,980,486 A | 11/1999 | Enger |
| 5,984,945 A | 11/1999 | Sirhan |
| 6,030,369 A | 2/2000 | Engelson et al. |
| 6,106,487 A | 8/2000 | Duane et al. |
| 6,129,708 A | 10/2000 | Enger |
| 6,143,013 A | 11/2000 | Samson et al. |
| 6,190,358 B1 | 2/2001 | Fitzmaurice et al. |
| 6,193,685 B1 | 2/2001 | Goodin |
| 6,248,092 B1 | 6/2001 | Miraki et al. |
| 6,254,549 B1 | 7/2001 | Ramzipoor |
| 6,319,229 B1 | 11/2001 | Kim et al. |
| 6,344,029 B1 | 2/2002 | Estrada et al. |
| 6,346,093 B1 * | 2/2002 | Allman et al. ........... 604/167.06 |
| 6,361,529 B1 | 3/2002 | Goodin et al. |
| 6,368,302 B1 | 4/2002 | Fitzmaurice et al. |
| 6,398,799 B2 | 6/2002 | Kramer |
| 6,409,863 B1 | 6/2002 | Williams et al. |
| 6,475,187 B1 | 11/2002 | Gerberding |
| 6,503,223 B1 | 1/2003 | Sekido et al. |
| 6,520,951 B1 | 2/2003 | Carrillo, Jr. et al. |
| 6,524,285 B1 | 2/2003 | Sirhan |
| 6,554,795 B2 | 4/2003 | Bagaoisan et al. |
| 6,605,062 B1 | 8/2003 | Hurley et al. |
| 2003/0153934 A1 | 8/2003 | Gerberding |
| 2003/0153942 A1 | 8/2003 | Wang et al. |
| 2004/0176742 A1 | 9/2004 | Morris et al. |

* cited by examiner

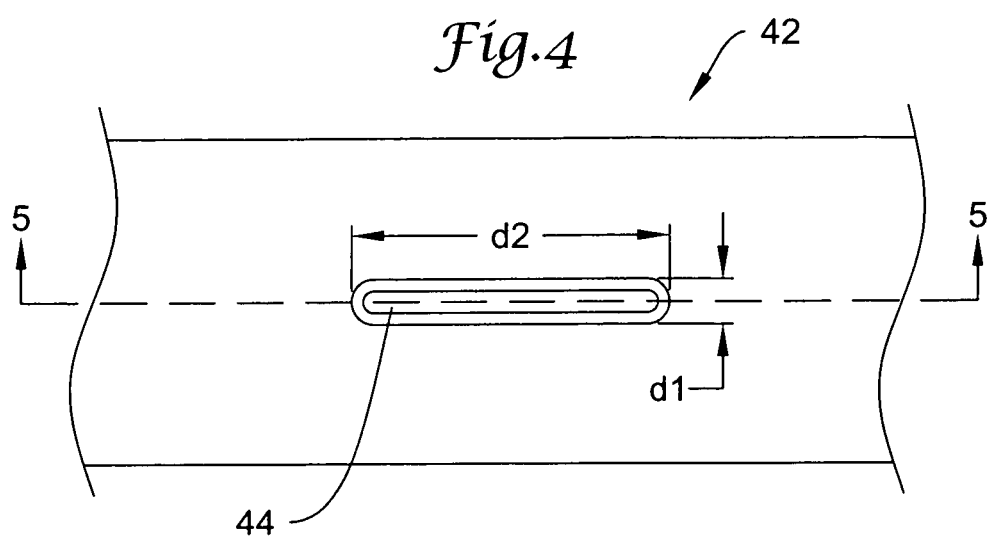
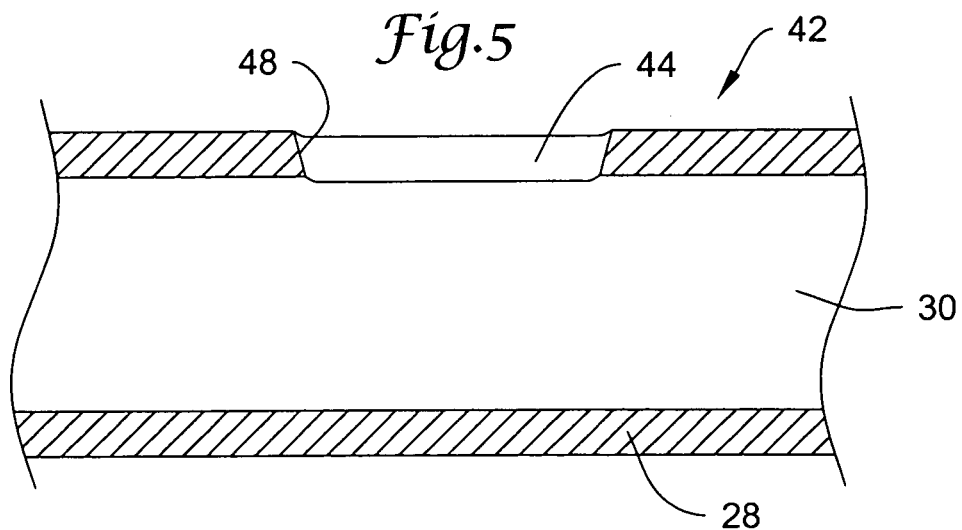
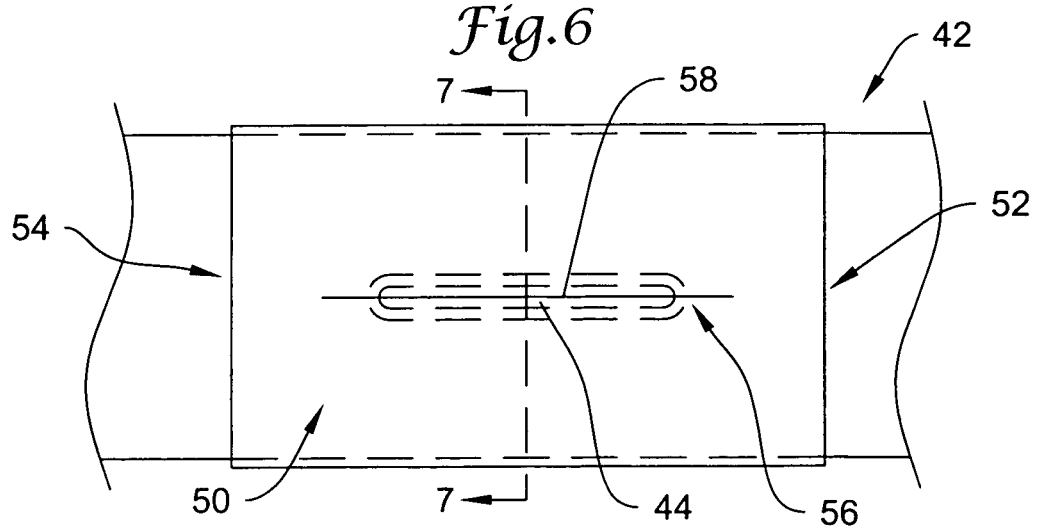

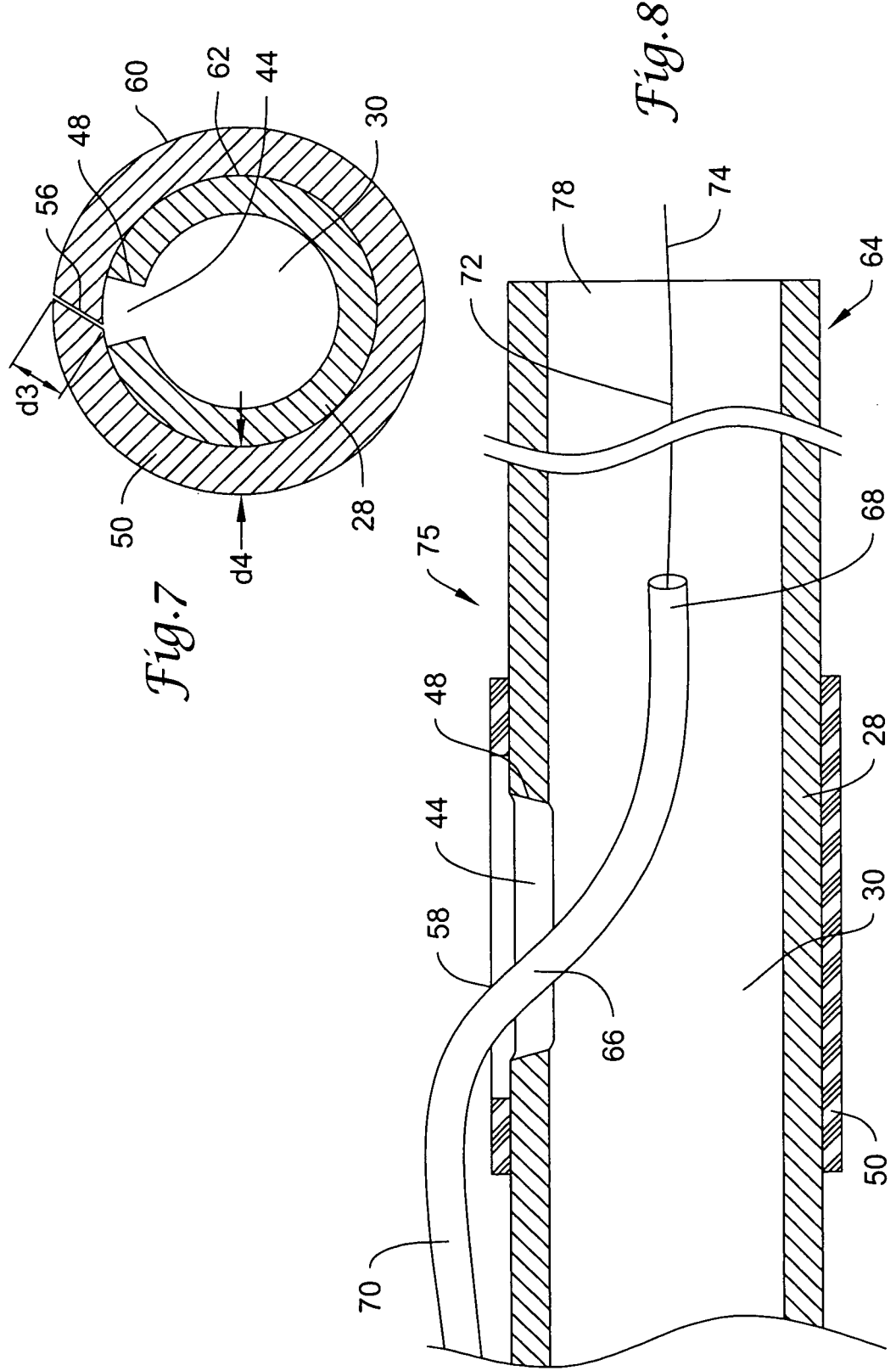

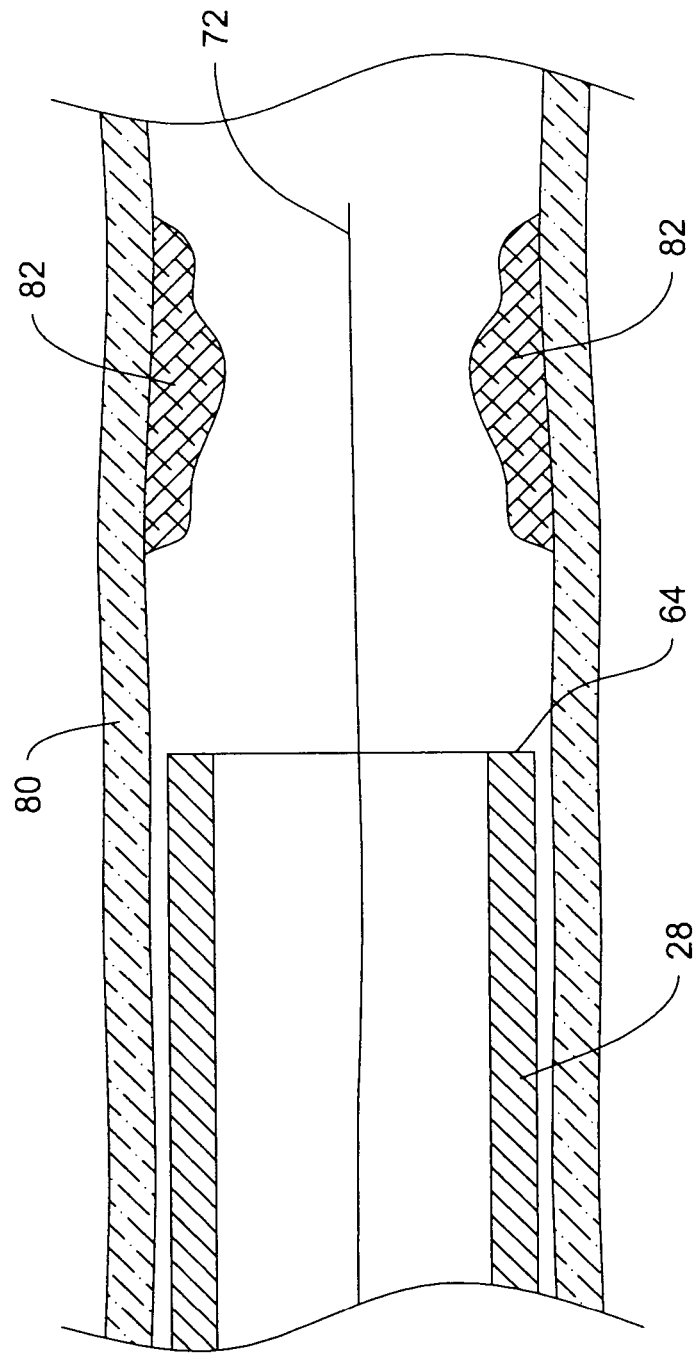

MICROCATHETER WITH SLEEVED GUIDEWIRE PORT

TECHNICAL FIELD

The present invention relates generally to catheters for delivery of therapeutic agents or devices to a site within a body lumen. More particularly, the present invention is directed to microcatheters used to navigate the neurovascular system.

BACKGROUND

A variety of intravascular catheters are known, including small diameter catheters that are configured for use in smaller vasculature such as the neurovasculature. Such catheters are known as microcatheters. Many microcatheters have a single lumen designed to accommodate a guidewire, treatment device or fluid that may be deployed through the single microcatheter lumen.

A need remains for improved microcatheters that preferably retain the single lumen yet can be deployed in rapid exchange fashion, while permitting device deployment or fluid passage through the central lumen while the rapid exchange proximal port allows guidewire passage into that same lumen. A need remains for a rapid exchange microcatheter having a central lumen that can remain substantially fluid tight when no guidewire is deployed through the microcatheter.

SUMMARY

The invention is directed to microcatheters that have a proximal guidewire port and a distal guidewire port. The proximal guidewire port can be positioned proximal of the distal end of the microcatheter, while the distal guidewire port can be positioned proximate the distal end of the microcatheter. The proximal guidewire port is located distal of the proximal end of the shaft to provide rapid exchange capability. The guidewire port can include a valve member that permits guidewire access through the catheter wall to a lumen of the microcatheter while providing a substantially fluid tight seal at least when the guidewire is not present in the guidewire port. Alternatively, the valve member can function to cover the port such that coils or other treatment means, such as a stent, do not catch on the port when advanced through the lumen.

Accordingly, an example embodiment of the invention can be found in a microcatheter that includes an elongate shaft that has a distal end, a proximal end and a lumen extending therebetween. In a preferred embodiment, the catheter includes a single lumen. A guidewire port can be positioned proximal of the distal end of the elongate shaft, and a control valve can be positioned exterior to the shaft lumen and overlying the guidewire port. The control valve can be configured to be moveable between a closed position and an open position with penetration of the control valve.

Another example embodiment of the invention can be found in a single lumen microcatheter having an elongate shaft that has a distal end and a proximal end. The elongate shaft can have an inner surface and an outer surface, and the inner surface can define a lumen that extends through the elongate shaft. A guidewire port can be positioned proximal of the distal end of the elongate shaft and can extend from the inner surface of the elongate shaft to the outer surface of the elongate shaft. A polymer sheath having an inner surface and an outer surface can be disposed over the guidewire port. The polymer sheath can include an angled slit that is in communication with the guidewire port. The angled slit can be configured to permit guidewire access through the guidewire port while remaining fluid tight when no guidewire is provided through the angled slit.

Another example embodiment of the invention can be found in a method of delivering a therapeutic element through a single lumen microcatheter. The microcatheter can include an elongate shaft, a guidewire port and a control valve disposed to overlay the guidewire port. A guidewire sheath can be advanced through the control valve and through the guidewire port. A guidewire can be advanced through the guidewire sheath, and the microcatheter can be advanced over the guidewire to a treatment site. Alternatively, the guidewire sheath may not be utilized, but instead, the guidewire is passed directly through the control valve. The guidewire and the guidewire sheath can be removed, thereby closing the guidewire port. The therapeutic element can be advanced or a therapeutic substance delivered through the elongate shaft, past the closed guidewire port, to the treatment site.

BRIEF DESCRIPTION OF THE FIGURES

FIG. 4 is a plan view of the 4-4 portion of FIG. 1;

FIG. 5 is a cross-sectional view of the microcatheter portion of FIG. 4, taken along line 5-5;

FIG. 6 shows FIG. 4, with the addition of a polymer sheath including a control valve;

FIG. 7 is a cross-sectional view of the microcatheter portion of FIG. 6, taken along line 7-7;

FIG. 8 is a partially sectioned view of the microcatheter portion of FIG. 5, showing a guidewire sheath and a guidewire disposed therein; and FIG. 9 is a partially sectioned view showing the distal portion of the microcatheter of FIG. 8 deployed within a patient's vasculature.

DETAILED DESCRIPTION

Figure 1:
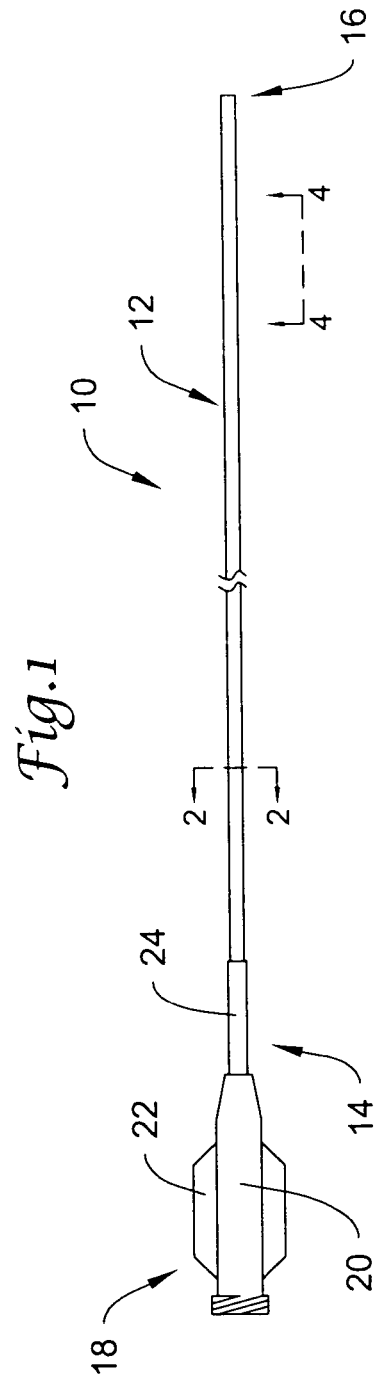
FIG. 1 is a plan view of a microcatheter in accordance with an embodiment of the invention.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the present invention. The catheter 10 can be one of a variety of different catheters, but is preferably an intravascular catheter. Examples of some intravascular catheters include microcatheters, drug delivery catheters, diagnostic catheters and guide catheters. As illustrated, FIG. 1 portrays a microcatheter, but the invention is not limited to such. Except as described herein, the intravascular catheter 10 can be manufactured using conventional techniques.

The intravascular catheter 10 can be sized in accordance with its intended use. The catheter 10 can have a length that is in the range of about 50 to 200 centimeters and can have a diameter that is in the range of about 1.7 F (French), but can be as large as about 12 F for certain applications.

In the illustrated embodiment, the intravascular catheter 10 includes an elongate shaft 12 that has a proximal end 14 and a distal end 16. A hub and strain relief assembly 18 can be connected to or disposed about the proximal end 14 of the elongate shaft 12. The hub and strain relief assembly 18 includes a main body portion 20, a pair of flanges 22 designed to improve gripping, and a strain relief 24 that is intended to reduce kinking. The hub and strain relief assembly 18 can be of conventional design and can be attached using conventional techniques.

Figure 2:
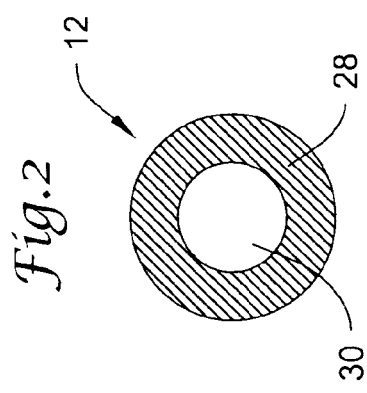
FIG. 2 is a cross-sectional view of the microcatheter of FIG. 1, taken along line 2-2.

FIG. 2 is a cross-sectional view of the elongate shaft 12, taken along line 2-2 of FIG. 1. A lumen 30 extends through the elongate shaft 12. As illustrated, the elongate shaft 12 is formed of a single polymer layer 28, which can be any suitable polymeric material such as a thermoplastic polymer material. The single polymer layer 28 can be extruded or otherwise formed from a single polymer or from a blend of polymers. The elongate shaft 12 can also include additional polymer layers.

Figure 3:
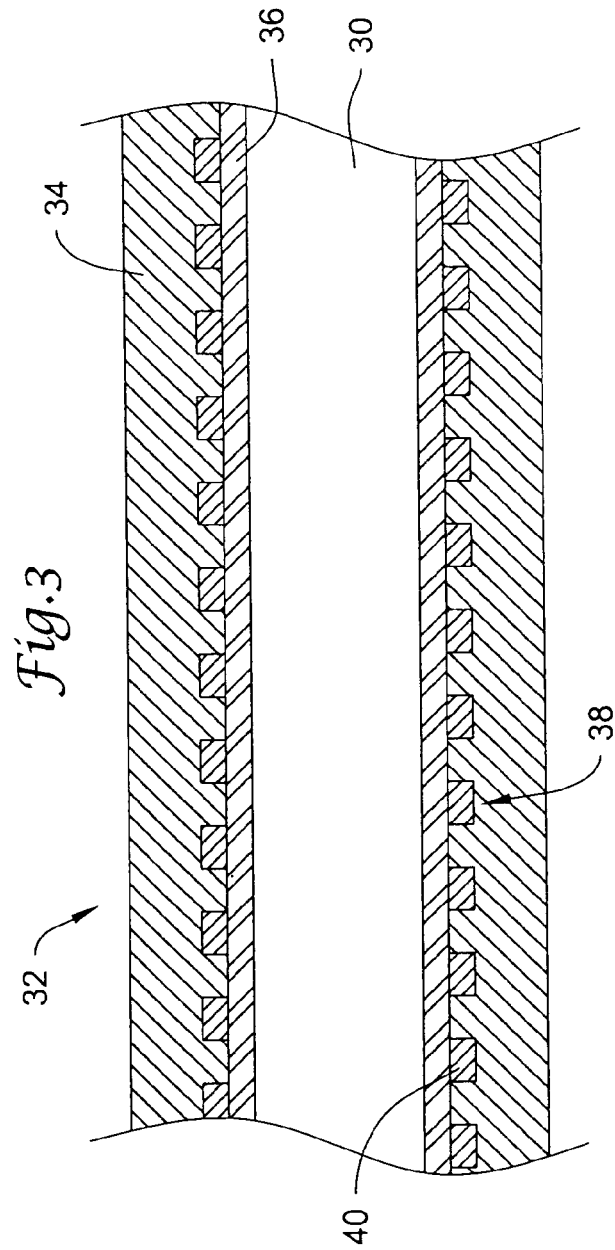
FIG. 3 is a partial longitudinal section view of a portion of a microcatheter, in accordance with an embodiment of the invention.

In particular, FIG. 3 illustrates a portion of another exemplary elongate shaft 32 that includes an outer polymer layer 34, an inner polymer layer 36, and an intermediate reinforcing layer 38. In some embodiments, the inner polymer layer 36 can be formed of or include a coating of a material having a suitably low coefficient of friction. Examples of suitable materials include polytetrafluoroethylene (PTFE), better known as TEFLON®. The inner layer 36 can be dimensioned to define a lumen 30 having an appropriate inner diameter to accommodate its intended use. In some embodiments, the inner layer 36 can define a lumen 30 having a diameter of about 0.0165 inches and can have a wall thickness of about 0.001 inches.

The outer polymer layer 34 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX), silicones, and co-polymers. The outer layer 34 can be a single polymer, multiple longitudinal sections or layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer, for example that available commercially under the ARNITEL® name, can be used. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing layer 38.

In some embodiments, the outer layer 34 of the shaft can have an inner diameter in the range of about 0.0165 inches to about 0.153 inches and an outer diameter in the range of about 0.023 inches to about 0.159 inches. Part or all of the outer layer 34 can include materials added to increase the radiopacity of the outer layer 34, such as 50% bismuth subcarbonate.

In some embodiments, a reinforcing layer 38 can be positioned between the inner layer 36 and the outer layer 34. A reinforcing braid layer 38 can be formed using a variety of different weave patterns, such as a three-over-three, a four-over-four, and the like. In some embodiments, in order to minimize impact on catheter diameter, the reinforcing layer 38 can be formed from braid wires or a single ribbon 40 or multiple ribbons that are helically wrapped around the inner layer 36.

The braid wires or ribbon 40 can have a rectangular, round, oval or other cross-sectional shape. In some embodiments, the braid wires or ribbon 40 can have a flat cross section such that it has a width that is at least about twice its height. The braid wires or ribbon 40 can be formed of any suitable material, such as stainless steel, tungsten, gold, titanium, silver, copper, platinum or iridium. The braid wires or ribbon 40 can also be formed from non-metallic material such as KEVLAR® (poly paraphenylene terephthalamide) fibers, LCP (liquid crystal polymer) fibers, or glass fibers and combinations thereof.

Turning now to FIGS. 4-7, a portion of an elongate shaft 42 is illustrated. In FIG. 4, a guidewire port 44 is illustrated as an elongate aperture having a radial width of D1 and an axial length of D2. D1 and D2 can be chosen to accommodate a particular size of guidewire and/or guidewire sheath, as will be discussed in greater detail hereinafter. The guidewire port 44 is preferably located between about 25 cm and about 40 cm from the distal end of the shaft. In some embodiments, the guidewire port 44 can have a width D1 of about 0.016 inches and a length D2 of about 0.24 inches. In other embodiments, the guidewire port 44 can have any other shape, such as a rectangular configuration or a round or oval configuration. In particular embodiments, the guidewire port 44 can have a substantially round configuration.

FIG. 5, which is a partially sectioned view taken along line 5-5 of FIG. 4, illustrates an example embodiment of a guidewire port 44 that can have a rectangular configuration. The guidewire port 44 has sides 48 that can taper inward toward the center of the guidewire port 44 in order to facilitate guidewire entry. The sides 48 can be angled at any useful angle. In some embodiments, the sides 48 can be angled at an angle of about 45 degrees with respect to a long axis of the elongate shaft 42. In some embodiments, the sides 48 can be substantially perpendicular to the long axis.

Turning now to FIG. 6, the elongate shaft 42 includes a polymer sheath 50 that can be positioned proximate to and overlying the guidewire port 44. The polymer sheath 50 has a distal portion 52 and a proximal portion 54. In this, proximal and distal merely refer to adjacent regions or sections of the elongate shaft 42 and thus can be found anywhere along the length of the elongate shaft 42.

The polymer sheath 50 can be formed of any suitable polymeric material. In some embodiments, the polymer sheath 50 can be formed of an elastic material such as polyurethane or silicone. The polymer sheath 50 can be about 0.0005 inches to about 0.002 inches thick. In some embodiments, the polymer sheath 50 can have an overall length that is about 0.25 inches to about 1.0 inches, sufficient to cover the elongate shaft 42 proximate the guidewire port 44. In other embodiments (not illustrated), the polymer sheath 50 can cover a greater portion, or even substantially all of the elongate shaft 42.

The polymer sheath 50 can be secured to the elongate shaft 42 using any suitable technique. For example, the polymer sheath 50 can be extruded over the elongate shaft 42, or the polymer sheath 50 can be heat-shrunk over the elongate shaft 42. Adhesive or thermal bonding can also be utilized.

The polymer sheath 50 includes a control valve 56 that can be configured to permit access through the polymer sheath 50 to the guidewire port 44 positioned beneath the polymer sheath 50. In some embodiments, the control valve 56 can be configured to permit a guidewire sheath and a guidewire (discussed hereinafter) to pass through the control valve 56 yet provide at least a substantially fluid-tight seal at least when there is not a guidewire or a guidewire sheath passing through the control valve 56. In an alternative embodiment, the control valve can be configured to be utilized with the guidewire alone, with no guidewire sheath. The control valve 56 can be configured such that fluid flow through the lumen 30 biases the control valve 56 into its closed position. The control valve 56 can also be configured to provide at least a substantially fluid-tight seal against a guidewire or guidewire sheath when passed therethrough. It is recognized that the polymer sheath/control valve can provide both disclosed functions.

In some embodiments, the control valve 56 can be formed to include an elongate slit 58 within the polymer sheath 50. The slit 58 can be formed having a length that is at least equal to one-half of the circumference of any guidewire or guidewire sheath that will be passed through the slit 58. The slit 58 can also be longer. In some embodiments, the slit 58 can be formed simply by cutting a slice into the polymer sheath 50 and can have a width of about 0.002 inches and a length of about 0.24 inches. The slit 58 can be formed using any suitable cutting means, including a knife or a laser.

As illustrated in FIG. 7, the slit 58 preferably extends from an outer surface 60 of the polymer sheath 50 to an inner surface 62 of the polymer sheath 50. In some embodiments, the slit 58 can extend through the polymer sheath 50 at an angle that is substantially perpendicular to the outer surface 60 of the polymer sheath. This is especially useful when placing embolic coils or stents. In particular embodiments, as illustrated, the slit 58 can extend through the polymer sheath 50 at an angle that is significantly less than about 90 degrees to the outer surface. In some embodiments, the slit 58 can extend through the polymer sheath 50 at an angle that is about 45 degrees from perpendicular.

If the slit 58 is formed at an angle other than perpendicular to the outer surface 60 of the polymer sheath 50, the slit 58 will have a depth D3 that is greater than a thickness D4 of the polymer sheath 50. As a result, adjacent portions of the polymer sheath 50 (on either side of the slit 58) that contact each other when nothing is passed through the control valve will have increased surface area. In some embodiments, this can result in greater sealing and can provide greater resistance to inadvertently opening the slit 58 when not desired. Fluid passed through the lumen can add pressure that assists in sealing the valve.

In some embodiments, a degree of MRI compatibility can be imparted. For example, to enhance compatibility with Magnetic Resonance Imaging (MRI) machines, it may be desirable to make any metallic portions of the catheter 10, such as the reinforcing layer 38, in a manner that would impart a degree of MRI compatibility. For example, the catheter 10, or portions thereof, can be made of a material that does not substantially distort the image and create substantial artifacts (artifacts are gaps in the image). Certain ferromagnetic materials, for example, may not be suitable because they may create artifacts in an MRI image. Suitable materials include, for example, tungsten, Elgiloy, MP35N, nitinol, and the like, and others.

In some embodiments, part or all of the catheter 10 can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding and solubility. In some embodiments, a distal portion of the catheter can be coated with a hydrophilic polymer, while the more proximal portions can be coated with a fluoropolymer.

Use of the microcatheter 10 described herein can be explained with reference to FIGS. 8 and 9. A microcatheter 75 has a distal end 64. As illustrated, the microcatheter 75 is formed with the polymer layer 28 defining the lumen 30 extending therethrough. A control valve including a polymer sheath 50 can be positioned over the microcatheter 75 such that the slit 58 is proximate to and overlying the guidewire port 44.

A guidewire sheath 66 having a distal end 68 and a proximal end 70 can be formed of any suitable polymeric material, such as polytetrafluoroethylene (PTFE), having a length of about 25 to about 160 cm and a diameter of about 1.25 F. The guidewire sheath is of sufficient length to extend outside the body in use so that it can be removed. Alternatively, the guidewire sheath can be of shorter length with a pull wire or other longitudinal member that is affixed near the guidewire sheath proximal end. The pull wire or other longitudinal member can then extend proximally outside the body to provide means for removing the guidewire sheath.

The distal end 68 of the guidewire sheath 66 can be advanced through the slit 58, through the guidewire port 44, and into the lumen 30. The guidewire sheath 66 can be advanced sufficiently far into the lumen 30 to guide the guidewire 72. Once the guidewire sheath 66 has been positioned, the guidewire 72 having a distal end 74 and a proximal portion 76 can be loaded by advancing the distal end 74 through the guidewire sheath 66 and into the lumen 30. The guidewire 72 can be advanced until the distal end 74 of the guidewire 72 extends through the distal end 64 of the microcatheter 75. The distal end 64 of the microcatheter 75 can include a distal guidewire port 78.

Once the guidewire 72 is thus loaded into the guidewire port 44 and out the distal guidewire port 78, the guidewire sheath 66 can, if desired, be removed. The guidewire 72 can be advanced into and through a patient's vasculature 80 (FIG. 9) until the distal end 74 of the guidewire 72 has reached and passed a treatment site of interest 82. After positioning the guidewire 72, which can include the use of radiopaque materials either within or on the distal end 74 of the guidewire 72, the microcatheter 75 can be advanced over the guidewire 72 to reach the treatment site 82. The guidewire 72 can than be withdrawn proximally until the guidewire 72 has been completely withdrawn from the microcatheter 76 and, if desired, from the body.

Once the guidewire 72 has been withdrawn, the control valve 56 can close, thereby rendering the microcatheter 75 at least substantially fluid tight. It is also recognized that the present catheter can be utilized in certain applications without the guidewire sheath. In these applications, the guidewire alone passes through the slit of the control valve. As a result, treatment elements such as embolic fluid or other treatment fluids can be passed through the microcatheter 75 to the treatment site 82. Suitable treatment elements also include, but are not limited to, stents, coils, embolic material and glue.

It should be understood that this disclosure is, in many respects, only illustrative. Changes may be made in details, particularly in matters of shape, size, and arrangement of steps, without exceeding the scope of the invention. The invention's scope is, of course, defined in the language in which the appended claims are expressed.

What is claimed is:

1. A single lumen microcatheter, comprising:
    an elongate shaft having a distal end and a proximal end, the elongate shaft having an outer surface and an inner surface, the inner surface defining a single lumen extending from the proximal end to the distal end of the elongate shaft and fluidly connecting the proximal end to an opening at the distal end of the elongate shaft;
    an elongate guidewire port positioned proximal of the distal end of the elongate shaft, the elongate guidewire port extending from the inner surface of the elongate shaft to the outer surface of the elongate shaft; and
    a polymer sheath disposed over the elongate guidewire port, the polymer sheath having an inner surface and an outer surface, the polymer sheath having a length measured from a proximal end of the polymer sheath to a distal end of the polymer sheath, the polymer sheath including a passage comprising an angled slit extending radially through the polymer sheath at an angle such that the slit has a depth that is greater than a thickness of the polymer sheath, the slit disposed parallel to a longitudinal axis of the elongate shaft, the slit having a length measured parallel to the length of the polymer sheath and parallel to the longitudinal axis of the elongate shaft, the length of the slit being less than the length of the polymer sheath such that the slit extends along only a portion of the length of the polymer sheath, the passage in communication with the elongate guidewire port, wherein the passage is configured to permit guidewire access through the elongate guidewire port while remaining substantially fluid tight in use when no guidewire is provided through the passage; and
    wherein when no guidewire is provided through the passage, the single lumen is substantially fluid tight from the proximal end of the elongate shaft to the opening at the distal end of the elongate shaft.

2. The single lumen microcatheter of claim 1, wherein the angled slit extends radially through the polymer sheath at an angle substantially less than 90 degrees to the outer surface of the polymer sheath.

3. The single lumen microcatheter of claim 1, wherein the angled slit extends from the outer surface of the polymer sheath to the inner surface of the polymer sheath.

4. The single lumen microcatheter of claim 1, wherein the angled slit is configured to accept both a guidewire and a sheath wherein the sheath is configured to accept the guidewire therein.

5. A method of delivering a therapeutic element through a single lumen microcatheter, the single lumen microcatheter comprising an elongate shaft, a guidewire port, and a control valve disposed proximate the guidewire port, the method comprising:
    advancing a guidewire sheath through the control valve and through the guidewire port;
    advancing a guidewire through the guidewire sheath;
    advancing the microcatheter over the guidewire to a treatment site;
    removing the guidewire and the guidewire sheath, thereby closing the guidewire port; and
    advancing the therapeutic element through the shaft, past the closed guidewire port, to the treatment site.

6. The method of claim 5, wherein the therapeutic element comprises embolic fluid.

7. The method of claim 5, wherein the therapeutic element comprises a mechanical device selected from the group consisting of stents, embolic coils, or other embolic material.

8. The single lumen microcatheter of claim 1 wherein the guidewire port has a length and a width, wherein the length is at least three times greater than the width.

9. The single lumen microcatheter of claim 8, wherein the length is at least six times greater than the width.

10. The single lumen microcatheter of claim 8, wherein the guidewire port has a first wall and a second wall, wherein the first wall and the second wall extend parallel to the longitudinal axis of the elongate shaft and wherein the guidewire port length also extends parallel to the longitudinal axis of the elongate shaft.

11. The single lumen microcatheter of claim 1, wherein the slit has a length greater than the length of the guidewire port.

12. The single lumen microcatheter of claim 1, wherein the guidewire port is defined by a perimeter wall having sides that tapers inward such that the perimeter of a top edge of the guidewire port is greater than the perimeter of a bottom edge of the guidewire port.

13. The single lumen microcatheter of claim 12, wherein the sides are angled at approximately a 45-degree angle.

14. A microcatheter, comprising:
    an elongate shaft having a distal end and a proximal end, the elongate shaft having an annular wall defining an outer surface and an inner surface of the elongate shaft, the inner surface defining a lumen extending through the elongate shaft fluidly connected to an opening at the distal end of the elongate shaft;
    an elongate guidewire port positioned proximal of the distal end of the elongate shaft, the elongate guidewire port extending through the annular wall of the elongate shaft from the inner surface of the elongate shaft to the outer surface of the elongate shaft; and
    a polymer sheath disposed over the elongate guidewire port, the polymer sheath having a wall defining an inner surface and an outer surface of the polymer sheath, the wall having a thickness measured from the inner surface to the outer surface of the polymer sheath, the polymer sheath including a passage comprising an angled slit extending radially through the wall of the polymer sheath from the outer surface to the inner surface of the polymer sheath, the angled slit extending at an angle such that the slit has a depth measured from the inner surface to the outer surface of the polymer sheath that is greater than the thickness of the wall of the polymer sheath, the slit disposed parallel to a longitudinal axis of the elongate shaft, the slit being defined between a first edge of the polymer sheath and a second edge of the polymer sheath facing the first edge, each of the first edge and the second edge extending from the outer surface to the inner surface of the polymer sheath, wherein the first edge and the second edge are in contact with each other when no guidewire is extended through the passage, the passage in communication with the elongate guidewire port, wherein the passage is configured to permit guidewire access through the elongate guidewire port while remaining substantially fluid tight in use when no guidewire is provided through the passage.

15. The microcatheter of claim 14, wherein the angled slit extends radially through the polymer sheath at an angle substantially less than 90 degrees to the outer surface of the polymer sheath.

\* \* \* \* \*